(12) United States Patent
Karlsson

(10) Patent No.: US 9,168,732 B2
(45) Date of Patent: Oct. 27, 2015

(54) METHOD FOR IMPARTING DIFFERENT VISUALLY DETECTABLE FEATURES TO A PLURALITY OF ITEMS, AND A PACKAGE COMPRISING ITEMS EACH HAVING A DIFFERENT VISUALLY DETECTABLE FEATURE

(75) Inventor: Elisabeth Karlsson, Kungsbacka (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/368,051

(22) PCT Filed: Dec. 21, 2011

(86) PCT No.: PCT/SE2011/051553
§ 371 (c)(1),
(2), (4) Date: Jun. 23, 2014

(87) PCT Pub. No.: WO2013/095224
PCT Pub. Date: Jun. 27, 2013

(65) Prior Publication Data
US 2015/0000541 A1    Jan. 1, 2015

(51) Int. Cl.
| | | |
|---|---|---|
| *B41F 17/00* | (2006.01) | |
| *B41M 1/24* | (2006.01) | |
| *B41M 1/26* | (2006.01) | |
| *B41M 1/30* | (2006.01) | |

(Continued)

(52) U.S. Cl.
CPC ........... *B41F 17/00* (2013.01); *A61F 13/15731* (2013.01); *A61F 13/551* (2013.01); *B41F 19/02* (2013.01); *B41M 1/24* (2013.01); *B41M 1/26* (2013.01); *B41M 1/30* (2013.01); *A61F 2013/4708* (2013.01); *A61F 2013/8497* (2013.01)

(58) Field of Classification Search
CPC ........................................................ B41M 1/24
USPC ............................................................ 101/32
See application file for complete search history.

(56) References Cited

U.S. PATENT DOCUMENTS

| | | | |
|---|---|---|---|
| 6,558,499 B1 | 5/2003 | Pargass et al. | |
| 6,837,958 B2 * | 1/2005 | Otsubo et al. ................. | 156/259 |

(Continued)

FOREIGN PATENT DOCUMENTS

| | | |
|---|---|---|
| EP | 1884360 A2 | 2/2008 |
| JP | H05-317357 A | 12/1993 |

(Continued)

*Primary Examiner* — Anthony Nguyen
(74) *Attorney, Agent, or Firm* — Drinker Biddle & Reath LLP

(57) ABSTRACT

A method of continuously imparting different visually detectable features to a plurality of items using a printing and/or embossing roll is provided. The circumference of the roll differs from the whole number of the item lengths. In a production series, the number of items each having a different visually detectable feature provided before said visually detectable features repeat themselves is greater than the number of items imparted after one full turn of the roll. Also disclosed is a package including a plurality of items each having a visually detectable feature that is different from the visually detectable features of all other items within the package, such that a first item includes a first visually detectable feature, and a second item includes a second visually detectable feature including at least a portion of the first visually detectable pattern element, wherein the first and second visually detectable features are different.

9 Claims, 8 Drawing Sheets

(51) Int. Cl.
  *A61F 13/551* (2006.01)
  *A61F 13/15* (2006.01)
  *B41F 19/02* (2006.01)
  *A61F 13/47* (2006.01)
  *A61F 13/84* (2006.01)

(56) References Cited

U.S. PATENT DOCUMENTS

| | | |
|---|---|---|
| 2004/0143231 A1 | 7/2004 | Nair et al. |
| 2005/0153100 A1* | 7/2005 | Zoller et al. ............... 428/131 |
| 2006/0009744 A1 | 1/2006 | Erdman et al. |
| 2006/0135927 A1 | 6/2006 | Zander et al. |
| 2008/0294140 A1* | 11/2008 | Ecker et al. ............... 604/385.23 |
| 2010/0010464 A1* | 1/2010 | Nishitani et al. ......... 604/385.01 |
| 2010/0089264 A1 | 4/2010 | Warner |
| 2010/0297377 A1* | 11/2010 | McNeil et al. ................. 428/43 |
| 2011/0256996 A1* | 10/2011 | Palm et al. ......................... 493/8 |

FOREIGN PATENT DOCUMENTS

| | | |
|---|---|---|
| WO | WO-2004/064872 A2 | 8/2004 |
| WO | WO-2006/068673 A1 | 6/2006 |
| WO | WO-2010/042470 A1 | 4/2010 |

\* cited by examiner

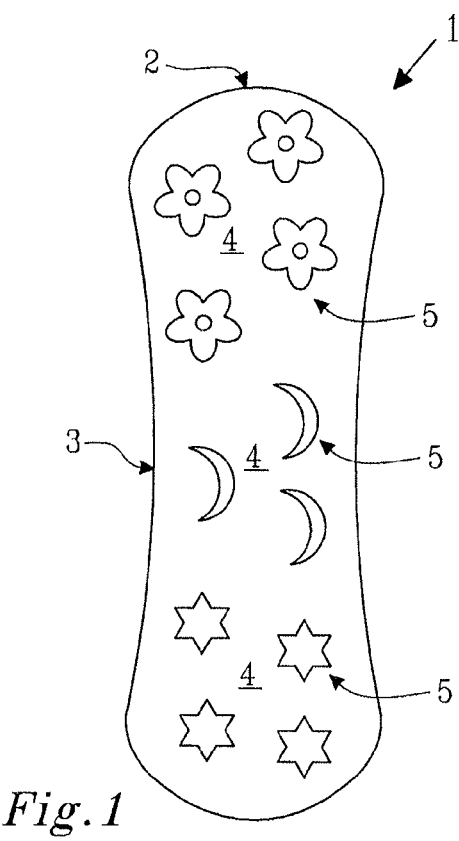
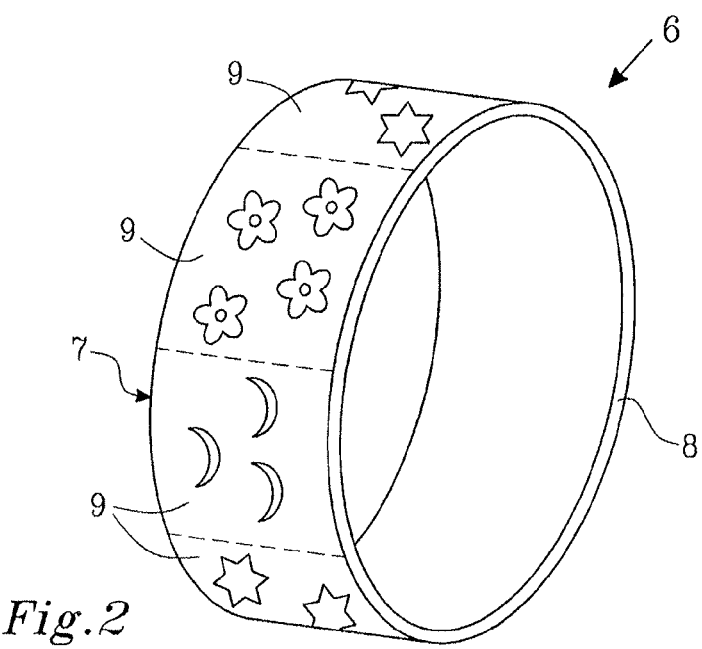
Fig.1
Fig.2

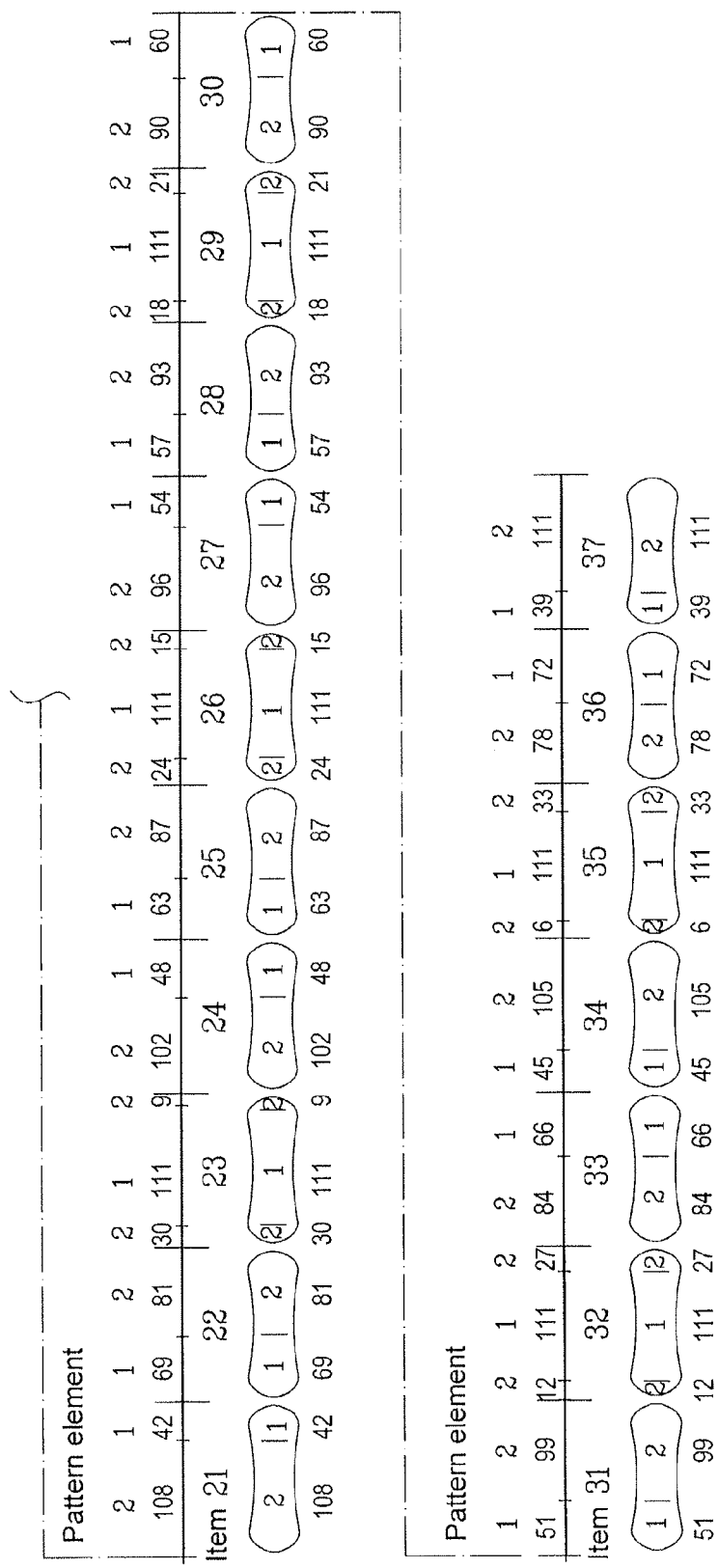
Fig.8-continue

METHOD FOR IMPARTING DIFFERENT VISUALLY DETECTABLE FEATURES TO A PLURALITY OF ITEMS, AND A PACKAGE COMPRISING ITEMS EACH HAVING A DIFFERENT VISUALLY DETECTABLE FEATURE

CROSS-REFERENCE TO PRIOR APPLICATION

This application is a §371 National Stage Application of PCT International Application No. PCT/SE2011/051553 filed Dec. 21, 2011, which is incorporated herein in its entirety.

TECHNICAL FIELD

The present disclosure relates to a method of continuously imparting different visually detectable features to a plurality of items. The disclosure also relates to a package including a plurality of items wherein each item within said package includes a visually detectable feature.

BACKGROUND

Absorbent products intended to absorb discharged body fluids are well known in the art. Such absorbent products generally comprise a fibrous mass or other absorbent body which can absorb and hold body fluids. The absorbent articles have included various systems of liquid-handling layers, such as intake layers, distribution layers, retention layers and the like. Additionally, the absorbent articles have included patterns of embossments distributed on the bodyside surface of the article to provide a hinging action, or to inhibit or direct a desired flow of liquids. Usually, in a given package of absorbent articles, every absorbent personal care article in the package has essentially the same embossing pattern.

Typically, the absorbent articles are placed in purses, backpacks, briefcases, and the like which do not always provide a hygienic environment for the articles, and thus the articles can become dirty and/or damaged. Further, the articles can become scattered about in purses, backpacks, briefcases, and the like so they are difficult to find when needed. Thus, in order to avoid these problems, personal care products are individually wrapped or are wrapped in groups of 2-5 absorbent articles in a pouch or similar wrapper. Typically, such wrappers have a solid colour, or have a pattern that covers the entirety of the wrapper and each wrapper within the packaging component is identical to each other.

Selecting a particular design for the personal care articles as well as the wrappers can be a deciding factor. While being liked by some consumers, other consumers may dislike the design. Those consumers who dislike the design may be more likely to complain about the product, or stop purchasing the product based on their dislike of the design.

In the case of feminine care products, such as sanitary napkins, incontinence pads, panty liners and the like, there is a need for an absorbent article which can provide a possible emotional benefit to the user. Many females experience a down turn in their mood during the menstrual period. Generally, sanitary napkins have a white colour or a simple combination of colours to provide a sanitary appearance. Within a given package of sanitary napkins, each sanitary napkin will look essentially identical to the other sanitary napkins in the package. As a result, the user of the sanitary napkins is provided with essentially no emotional benefit by the appearance of the sanitary napkin. Therefore, there is a need in the art to provide a possible emotional benefit to the users of the feminine care products.

In the case of diapers and incontinence protectors, the exterior of these disposable absorbent articles is covered with a flexible, liquid impervious member to prevent a leakage of absorbed liquids from the disposable absorbent articles. Such a liquid impervious member is generally referred to as a backsheet, and is often constructed from a liquid impervious material such as a polyethylene film, and, if desired, other outer cover material such as a nonwoven material. The backsheet constitutes the garment contacting surface of the absorbent articles.

It is also known that the garment contacting surface of the absorbent articles often has printed graphics to get a positive attention from the user or caregiver not only in use but also in the market. In the latter case, the absorbent articles are often contained in a package having a transparent portion such that the graphics are visible through the transparent portion. Such graphics are typically printed on either a landing zone material or a backsheet material. Graphics printed on the garment contacting surface of disposable absorbent articles can be preferred by consumers due to their entertaining functions.

Those graphics are typically printed by using conventional printing techniques such as gravure and flexography technologies which employ a printing plate to print the graphic on a sheet material, e.g. a backsheet material, a landing zone material, or a fastening tape material. The printing plate has ink images for graphics to be printed. The printing plate is typically mounted on a printing cylinder in a printing process. In the printing process, when the cylinder rotates, the printing plate transfer the ink images to the sheet material by contacting the sheet material thereby printing the graphics thereon.

The number of the ink images which can be prepared using a given cylinder depends on the sizes of the ink images in relation to the size of the cylinder. In general, since the size of the landing zone member is not large, the size of the ink images prepared in the printing plate tends to be small. On the other hand, since the size of the backsheet is relatively large, the size of the repeated ink images tends to be large. The number of the graphics to be printed is thus limited in particular for a relatively large component material of disposable absorbent articles such as a backsheet material. Because of the above reasons, the variety of the graphics printed on conventional disposable absorbent articles is limited in one package.

Thus, it is understood that this limitation results in preventing users or consumers from enjoying more variety of graphics in the disposable absorbent articles packed or contained in one package.

Several attempts have been made in order to overcome such a limitation, and to provide a method for printing or embossing a large number of different graphics.

WO 2006/068673 suggests a package wherein every absorbent article and/or a wrapper component may have a different pattern embossed or printed on the body facing surface or the garment facing surface of each of the absorbent articles.

According to WO 2006/068673, the different embossing patterns on the absorbent personal care articles or the wrapper components may be imparted in many different ways, including using side-by-side production lines, a single production line with separate embossing sections, i.e. a single line splitting into two or more lines to emboss the absorbent personal care articles or the wrapper components, using a single process line and preparing the absorbent personal care articles or the wrapper components in a batch process, changing the embossing roll after each batch of absorbent personal care articles or the wrapper components, or a single production line and using an embossing roll with a long repeat pattern. By a long repeat pattern, it is meant that several absorbent personal care articles or the wrapper components are embossed before the pattern repeats itself. This can be accomplished by using, for example, a large diameter embossing roll. Other types of embossing rolls, such as embossing rolls with several different patterns across the width of the roll may also be used.

WO 2010/042470 suggests a process and apparatus for printing a series of different graphics on substrates used in the manufacture of absorbent articles. Embodiments of the apparatuses and methods disclosed in WO 2010/042470 utilize flexographic printing to provide for a sequential manufacture of a series of n absorbent articles having different graphics printed thereon, wherein n can be a number of 2 or greater. In addition, an absorbent product may be produced by placing one or more, or a portion, of the series of n absorbent articles in a package.

An apparatus of WO 2010/042470 for printing disposable absorbent articles includes: a central impression cylinder defining an outer circumferential surface; and a plurality of printing stations positioned adjacent the outer circumferential surface of the central impression cylinder. Each printing station includes: a printing roller; an endless belt having a first surface and a second surface opposite the first surface, wherein the second surface partially surrounds the printing roller and wherein the printing roller is adjacent the central impression cylinder so as to define a nip between the first surface of the endless belt and outer circumferential surface of the central impression cylinder; a first plurality of n printing patterns operably disposed on the first surface of the endless belt, wherein n is 2 or greater; an ink supply; and an anilox roller operably connected with the ink supply and the endless belt wherein the anilox roller is adapted to deposit ink from the ink supply onto the first plurality of n printing plates.

EP 1 884 360 discloses a printing unit comprising a plurality of plate rollers disposed in series along a path of the web material, so that said web material is decorated with a print obtained by the combination of designs printed by said plate rollers, wherein at least some of said plate rollers have printing plates with printing extensions of different lengths from one another, equal to multiples of the longitudinal dimension of the sheets into which the web material is divided and each of the plates has a plurality of motifs of a length equal to said longitudinal dimension. Moreover, on each printing plate there is provided at least one series of designs different from one another and the designs of the plates of said at least two rollers differ from one another at least in part.

WO 2004/064872 describes a method of printing a graphic on a component material for absorbent articles. The graphic data is stored in a graphic memory for printing n graphics, n being greater than 2; and then selected and printed by an ink jet on the sheet material. The process is repeated so that the n graphics are printed on the sheet material.

WO 2004/064872 also discloses a method of producing an absorbent product including a package and at least n absorbent articles contained in the package, wherein n is greater than 10. The method includes the steps of: (a) supplying a sheet material having a plurality of printing frames sequentially disposed along the machine direction, wherein each printing frame includes n graphics printed sequentially in the machine direction; (b) incorporating other component materials with the sheet material to form n absorbent articles in the machine direction, wherein each absorbent article have a corresponding graphic of the n graphics; (c) detecting the printing frame in the sheet material; (d) transporting the absorbent articles which are within the detected printing frame; and (e) packing the transported absorbent articles into one package.

JP 05317357 describes a method for making designs printed on the reinforcing sheet of paper diapers, such that the designs vary with the paper diapers. The method comprises providing a printing plate for printing the reinforcing sheet of paper diapers. The printing plate 9 is divided along its longitudinal direction per width S and different designs are printed on each division I-VIII so that the reinforcing sheet has different designs for each diaper.

US 2006/0009744 discloses decorative components of various sizes and uses for assembly into absorbent articles manufactured using a decorative component material. The absorbent articles have a variety of decorative appearances. A method for producing absorbent articles from the decorative component material comprises providing a roll of decorative component material comprising a design from which absorbent articles having a variety of desirable decorative appearances can be manufactured on a single assembly line. The roll of decorative component material may comprise one or more noncomprehensive designs that, upon assembly of a component made from the material into an absorbent article, provide a different decorative appearance to each successive article made in continuous assembly.

U.S. Pat. No. 6,558,499 discloses an absorbent article including one or more graphics thereon and a method for making the same, wherein the method comprises the step of attaching the cross-directional continuously moving discrete absorbent cores to the continuously moving appliqué layer such that a graphic corresponds to each of the cross-directional continuously moving discrete absorbent cores; cutting the continuously moving appliqué layer with the attached cross directional continuously moving absorbent cores at a predetermined position between said cross directional continuously moving absorbent cores to form discrete absorbent articles, wherein each absorbent article in the set of absorbent articles has an appliqué layer and the appliqué layer includes a graphic.

All the above-mentioned methods have the disadvantage of requiring complicated and expensive production lines having low flexibility or rolls having a large diameter, which may deteriorate the manufacturing speed and requires additional space for the production line.

Hence, there is a need for a method that can provide a large number of different graphics imparted on absorbent articles, using an uncomplicated and inexpensive equipment.

SUMMARY

As used herein, the term "different" means that the visually detectable features are perceived as different by a user when the user looks at the visually detectable features using his/her usual attention. Thus, two visually detectable features having differences which are unintentionally caused by manufacturing variations or errors are not different from each other. Different visually detectable features are determined by, for example, different components constituting visually detectable features, different colours or colour combinations used in the visually detectable features or its components, different sizes of the visually detectable features or its components, the spatial orientation of the visually detectable features or its components, the geometrical shapes of the visually detectable features or its components, the number of the components in the visually detectable features, or the like.

By "item" is meant a single product imparted with a visually detectable feature according to the method. An item in the context of the present description may be an absorbent article such as a diaper, a sanitary napkin, a panty liner, an incontinence protector or the like; a wrapping sheet, such as a single wrap or easy wrap; or a release liner.

By "visually detectable element" is meant a portion of the roll having a pattern, a symbol, an object or a colour being different from the patterns, the symbols, the objects or the colours of other portions of the roll.

As used herein, the term "visually detectable pattern element" means a pattern, a symbol, an object or a colour transferred by means of the visually detectable element to the item.

By "visually detectable feature" is meant the composition of all the visually detectable pattern elements on one item. It is noteworthy that different visually detectable features may comprise at least portions of the same visually detectable pattern element.

A visually detectable feature may be a printed and/or embossed pattern, a printed and/or embossed image, a colour or a combination thereof.

Embossing of an item may be accomplished by any means know to those skilled in the art. For example, the item may be passed between a heated or unheated anvil roll and heated or unheated embossing roll, which is engraved with a relief embossing pattern. Other techniques known to those skilled in the art, including using ultrasonic embossing and the like may also be used to obtain the desired embossing effect.

Printing may also be used to impart a pattern to the item, such as any contact printing method known to the person skilled in the art.

Disposable absorbent articles such as, for example, feminine care and incontinent absorbent products, generally include a liquid pervious topsheet, a substantially liquid impervious backsheet, and an absorbent core positioned and held between the topsheet and the backsheet. Disposable absorbent articles may also include other optional components or layers, such as liquid wicking layers, liquid distribution layers, barrier layers, and the like, as well as combinations thereof, which may improve the fluid handling and storage properties of the disposable absorbent article. Generally, disposable absorbent articles provide a body-facing surface and a garment-facing surface. The body-facing surface is generally the topsheet and garment facing surface is the backsheet. The visually detectable features may be present on any component of the absorbent article.

The wrapping sheet is intended to protect the absorbent article from outer factors such as dirt and damage. The wrapping sheet may contain one or several absorbent articles. The material of the wrapping sheet may be any material known in the art, such as polyethylene or propylene film, a nonwoven material, or a laminate of a nonwoven material and a plastic film. The visually detectable feature may be present on the outer and/or the inner side of the wrapping material, or between the layers if several layers are present.

Release liner is a component provided for protection of the adhesive provided on the garment-facing sheet of absorbent article. The release liner can be of any material known in the art, e.g. silicone-coated paper. The visually detectable feature may be present on one or both sides of the release liner.

In certain embodiments, the method for continuously imparting different visually detectable features to a plurality of items, comprises the steps of:
providing a plurality of items for imparting said different visually detectable features;
providing a roll including a plurality of different visually detectable elements;
imparting said visually detectable features to said plurality of items by means of said visually detectable elements on said roll.

In certain embodiments, the method is characterized in that the circumference of said roll is not equal to a whole number of the item lengths, i.e. the length of one item multiplied by an integer. This can be expressed by equation (1):

$$L \neq N_1 \cdot L_0 \tag{1}$$

wherein L is the circumference of the roll, $N_1$ is an integer and $L_0$ is the length of one item.

In further embodiments, the method is further characterized in that in a production series the number of items each having a different visually detectable feature provided before said visually detectable features repeat themselves is greater than n, wherein n is calculated as:

$$n = \frac{L}{L_0} \tag{2}$$

According to further embodiments, the number of items each having a different visually detectable feature provided before the pattern sequence of the visually detectable features starts to repeat itself is greater than the number of items imparted after one full turn of the roll. In other words, the method allows producing a large amount of items each having a different visually detectable feature using a roll having quite a small diameter. This is explained in greater detail below.

The roll may be an embossing roll, a printing roll, or an embossing and printing roll. The surface of the roll is provided with at least one visually detectable element. A visually detectable element may be a geometric or graphic pattern, a single geometric or graphic figure, a symbol or character, a coloured portion, a text message, an embossing pattern, an embossing figure or the like.

According to certain embodiments, the roll may include at least one first visually detectable element having a length equal to the length of the item, and at least one second visually detectable element having a length different from the length of the item, wherein said first and said second visually detectable elements are different. The first item imparted by such a roll will be provided with a first visually detectable feature including a first visually detectable pattern element corresponding to the first visually detectable element. The next (second) item will be provided with a second visually detectable feature including a second visually detectable pattern element corresponding to the second visually detectable element on the roll.

Assuming now that the length of the second visually detectable element is shorter than the length of the second item, the visually detectable feature of the second item will also include a portion of the first visually detectable pattern element. The subsequent item will be provided with a visually detectable feature including a portion of the first visually detectable pattern element and a portion of the second visually detectable pattern element.

If the length of the second visually detectable element is longer than the length of the second item, the third item will be provided with a visually detectable feature comprising a portion of the second visually detectable pattern element, and a portion of the first visually detectable pattern element. The subsequent fourth item will be provided with a visually detectable feature including a portion of the first visually detectable pattern element and a portion of the second visually detectable pattern element, such that the visually detectable feature of the third item is different from the visually detectable feature of the fourth item. The process continues until the lateral edge of the first visually detectable element coincides with the lateral edge of the item.

The roll may also include at least one first visually detectable element having a length different from the length of the item, and at least one second visually detectable element having a length different from the length of the item, wherein said first and said second visually detectable elements are different. Assuming that the lengths of the first and second visually detectable elements are shorter than the length of the item, the first item will be provided with a visually detectable feature including a portion of the first visually detectable pattern element and a portion of the second visually detectable pattern element. The second item will be provided with a visually detectable feature including a portion of the second visually detectable pattern element and a portion of the first visually detectable pattern element. The subsequent third item will be provided with a visually detectable feature including a portion of the first visually detectable pattern element and a portion of the second visually detectable pattern element, such that the visually detectable feature of the third item is different from the visually detectable features of preceding and following items.

Regardless of the lengths of the visually detectable elements, the imparting process providing items having different visually detectable features continues until the lateral edge of the first visually detectable element coincides with the lateral edge of an item, and the sequence of the visually detectable features recommences.

In an aspect, a roll creates a dislocation in the position of the printed and/or embossed visually detectable pattern element from one item to another. Thus, a plurality of items each having a different visually detectable feature is produced. After a certain number of turns, the dislocation, after having travelled a distance, will be positioned such that the lateral edge of the first visually detectable element coincides with the lateral edge of an item such that the sequence of visually detectable elements constituting a visually detectable feature starts to repeat itself.

Of course, it is useful to be able to predict and determine the number of items Q each having a different visually detectable feature provided before said visually detectable features repeat themselves in a production series. This amount Q is calculated as:

$$Q = \frac{L}{x} \cdot a \quad (3)$$

$$x = L - N_2 \cdot L_0 \text{ if } L > L_0 \quad (4')$$

$$x = L_0 - L \text{ if } L < L_0 \quad (4'')$$

$$N_3 = \frac{L_0}{x} \cdot a \quad (5)$$

$$N_2 = \left\lfloor \frac{L}{L_0} \right\rfloor \quad (6)$$

wherein L is the circumference of the roll, $N_2$ and $N_3$ are integers, $L_0$ is the length of one item, and a is the smallest integer needed to satisfy equation (5).

In other words, x is the difference between a given circumference L of the roll and the largest possible whole number of item lengths on the roll circumference if $L>L_0$ (eq. (4')). In cases when $L<L_0$, x is the difference between the length of the item and the circumference of the roll (eq. (4")).

When x is determined, factor $L_0/x$ is calculated (eq. (5)). If $L_0/x$ is an integer, factor a is set to 1. If the resulting value is not an integer, it is multiplied by factor a, such that an integer $N_3$ is obtained. Factor a is the smallest possible integer.

Having determined factor a, the number of items Q each having a different visually detectable feature provided before said visually detectable features repeat themselves in a production series can be calculated according to eq. (1). Examples of such calculations are given below.

As mentioned above, the method relies on the fact that the roll provides a displacement of the sequence of the visually detectable pattern elements after each full turn of the roll. Thus, a production series provided according to embodiments of the method includes a first item including a first visually detectable feature being provided by at least a portion of a first visually detectable element on said roll, and a second item including a second visually detectable feature being provided by at least a portion of said first visually detectable element on said roll, wherein said first and second visually detectable features are different. In other words, due to the displacement, different portions of the same visually detectable pattern element may be present on two items, which makes the visually detectable feature of the first item different from the visually detectable feature of the second item.

In certain embodiments, the method may be used for imparting visually detectable features to items such as absorbent articles such as diapers, sanitary napkins, panty liners, incontinence protectors or the like. The items may also be wrapping sheets, such as single wraps or easy wraps. Further, the method may be used for imparting items such as release liners.

In cases when the method is used for imparting a visually detectable feature on an absorbent article, said visually detectable feature may be provided on at least one component of said absorbent article, such as a topsheet, a backsheet, a protective layer, an acquisition layer or an absorbent element.

The visually detectable feature may also be provided on at least two components of said absorbent article, for example, on the topsheet and the backsheet, such that said visually detectable feature on the first component is different from said visually detectable feature on the second component.

The items produced using methods according to methods described above will thus each have different visually detectable features. The items of a production series may then be placed in a package including a plurality of items wherein each item within said package includes a visually detectable feature, wherein said visually detectable feature includes at least one visually detectable pattern element, said visually detectable feature of each of said items is different from the visually detectable features of all other items within said package. The package can include a first item including a first visually detectable feature including at least a portion of a first visually detectable pattern element, and a second item includes a second visually detectable feature including at least a portion of said first visually detectable pattern element, wherein said first and second visually detectable features are different.

As explained above, due to the displacement of each visually detectable element after each full turn of the roll in relation to the lateral edges of the items to be imparted, the package can include at least two items having different visually detectable features such that said visually detectable features include portions of the same visually detectable pattern element. Despite the fact that the visually detectable features of these items will include portions of the same visually detectable pattern element, these portions will be different, and the spatial position of the portions will be different, which in turn means that the visually detectable features will be different.

A variety of visually detectable features within the same package has a certain emotional benefit for the user, since the user will be surprised by a new design at every change of item.

In certain embodiments, the package includes a plurality of items each having a different visually detectable feature. Each visually detectable feature in turn includes at least one visually detectable pattern element which may be a geometric or graphic pattern, a single geometric or graphic figure, a symbol or character, a coloured portion, a text message, an embossed pattern, an embossed figure or the like.

The package may contain absorbent articles such as diapers, sanitary napkins, panty liners, incontinence protectors or the like.

The items within the package may also be wrapping sheets, such as single wraps or easy wraps, or release liners.

In cases when the package includes absorbent articles, said visually detectable feature may be provided on at least one component of said absorbent article, such as a topsheet, a backsheet, an acquisition layer or an absorbent element.

The visually detectable feature may also be provided on at least two components of said absorbent article, for example, on the topsheet and the backsheet, such that said visually detectable feature on the first component is different from said visually detectable feature on the second component.

The person skilled in the art would understand that the number of items each having a different visually detectable feature may be varied depending on the character of the item, the size of the package and so on. The number of items each having a different visually detectable feature in a package may, for example, be between 10 and 50.

BRIEF DESCRIPTION OF THE DRAWINGS

Embodiments of the invention will now be described by way of example with reference to the accompanying drawings, of which:

FIG. 1 shows an absorbent article including a visually detectable feature provided by an embodiment of the method.

FIG. 2 shows a roll used in an embodiment of the method.

DETAILED DESCRIPTION OF PREFERRED EMBODIMENTS

Figure 3:
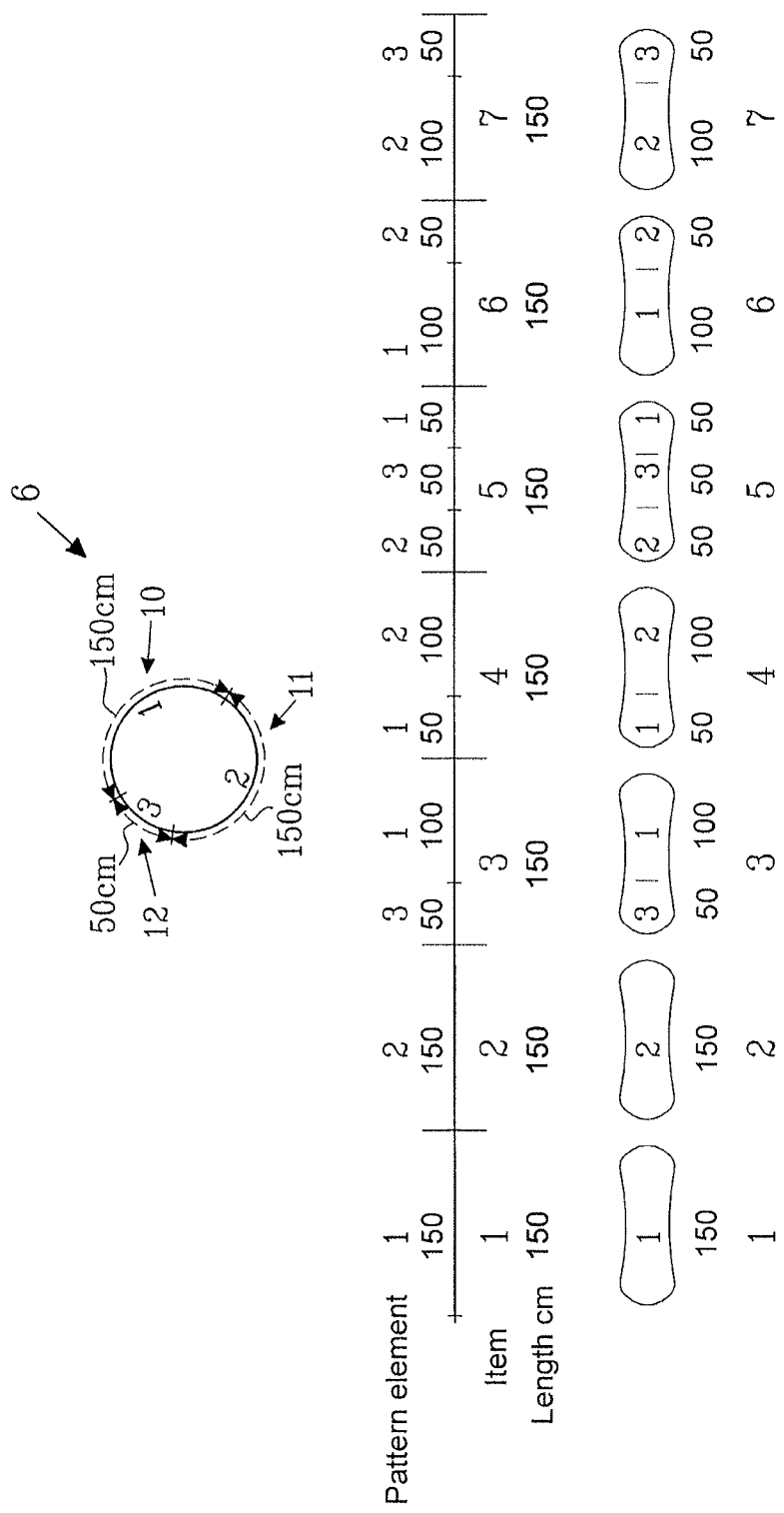
FIGS. 3-8 illustrate different embodiments of the roll and the pluralities of items provided using embodiments of the method.

FIG. 1 illustrates an absorbent article (1) including two lateral edges (2) and two longitudinal edges (3). In its simplest embodiment, the absorbent article (1) includes a liquid-permeable topsheet, a liquid-impermeable backsheet and an absorbent structure positioned between the topsheet and the backsheet. The absorbent article (1) further includes a visually detectable feature (5) provided using embodiments of the method. The absorbent article can be a diaper, a sanitary napkin, a panty liner, an incontinence protector, or any other kind known to the person skilled in the art.

As can be seen from FIG. 1, the visually detectable feature (5) includes three different visually detectable pattern elements (4), namely flowers, crescents and stars. It is understood that the number as well as the layout of visually detectable pattern elements (4) may be varied. For example, the visually detectable feature (5) may include a single visually detectable pattern element (4) or a plurality of visually detectable pattern elements (4). The visually detectable pattern element (4) may for example be a geometric or graphic pattern, a single geometric or graphic figure, a symbol or character, a coloured portion, a text message, an embossed pattern, an embossed figure or combinations thereof. In particular embodiments, the visually detectable pattern element (4) is designed such that it provides an emotional benefit to the user.

FIG. 2 illustrates a roll (6) for imparting different visually detectable features to a plurality of items. The roll may be a printing roll, an embossing roll or a combination of a printing and embossing roll, and includes an outer surface (7) and an inner surface (8). The outer surface of the roll (7) includes a portion including three visually detectable elements (7), in this case flowers, crescents and stars. When the outer surface (7) of the roll (6) comes in contact with the surface of the item (1) to be imparted, the visually detectable element (7) is transferred to the surface of said item (1), thus forming a corresponding visually detectable pattern element (4). It is essential that the circumference of the roll (6) L is not equal to a whole number of the item lengths $L_0$, i.e. the length of one item multiplied by an integer. This can be expressed by equation (1):

$$L \neq N_1 \cdot L_0 \quad (1)$$

wherein L is the circumference of the roll, $N_1$ is an integer and $L_0$ is the length of one item.

For example, if the length of one item $L_0$ is 150 cm, the circumference of the roll L may not be equal to 150*2=300 cm, 150*3=450 cm, 150*4=600 cm and so on.

In certain embodiments of the method, the number of items each having a different visually detectable feature provided in a production series before said visually detectable features repeat themselves is greater than n, wherein n is the largest possible whole number of the item lengths on the circumference of the roll and is calculated as:

$$n = \frac{L}{L_0} \quad (2)$$

For example, if the circumference of the roll L is 500 cm and the length of one item $L_0$ is 150 cm, the number of items each having a different visually detectable feature provided before said visually detectable features repeat themselves is greater than the largest integer less than or equal to 500/150=3.33, i.e. 3. This can also be written $\lfloor 500/150 \rfloor = 3$.

In other words, embodiments of the method provide the advantage of producing a large number of items each including different visually detectable features using a roll having relatively small diameter. This will now be described in greater detail using a number of examples.

Example 1

As may be seen from FIG. 3, the roll (6) of Example 1 includes three different visually detectable elements (10), (11), (12), having patterns designated 1, 2 and 3 respectively, wherein two of the visually detectable elements have a length of 150 cm, and the third visually detectable element have a length of 50 cm. The length of the item $L_0$ in Example 1 is 150 cm. Thus, the first and the second visually detectable elements have the same length as the length of the item, while the third visually detectable element has the length different from the length of the item.

The circumference of the roll is $$L = 150 + 150 + 50 = 350 \text{ cm}$$

According to equation (4')

$$x = 350 - 2 \cdot 150 = 50 \text{ cm}$$

To calculate factor a, equation (5) is used:

$$N_3 = \frac{150 \text{ cm}}{50 \text{ cm}} \cdot a$$

Since in this particular case 150/50 is an integer, factor a is 1.

Now, using equation (3), the number of items having different visually detectable features provided before the sequence of visually detectable features is repeated can be calculated:

$$Q = \frac{350}{50} \cdot 1 = 7$$

Indeed, as can be seen in FIG. 3, seven items each having a different visually detectable feature are provided using the roll of Example 1.

The first item will be imparted with the first visually detectable feature including visually detectable pattern element 1 provided by the first visually detectable element (10), since the length of the first visually detectable element (10) is the same as the length of the item. The second item will be imparted with the second visually detectable feature including visually detectable pattern element 2 provided by the second visually detectable element (11), since the length of the second visually detectable element (11) is the same as the length of the item. Here, the displacement in the sequence of the visually detectable pattern elements occurs. Thus, 50 cm of the third item will include visually detectable pattern element 3 provided by the third visually detectable element (12), and 100 cm of the third item will include visually detectable pattern element 1 provided by the first visually detectable element (10). Remaining 50 cm of the first visually detectable element (10) will impart the fourth item, followed by 100 cm of the second visually detectable element (11). The fifth item will be imparted with 50 cm of the second visually detectable element (11), 50 cm of the third visually detectable element (12), and 50 cm of the first visually detectable element (10). The subsequent sixth item will include 100 cm of visually detectable pattern element 1 provided by the first visually detectable element (10), and 50 cm of visually detectable pattern element 2 provided by the second visually detectable element (11). Finally, the seventh item will include 100 cm of visually detectable pattern element 2 provided by the second visually detectable element (11), and 50 cm of visually detectable pattern element 3 provided by the third visually detectable element (12). After the seventh item, the sequence of the visually detectable features is repeated.

Example 2

The roll of Example 2 includes three different visually detectable elements (13), (14) and (15). As may be seen from FIG. 4, the visually detectable elements (13), (14) and (15) have patterns designated 1, 2 and 3 respectively, and all the visually detectable elements have a length of 120 cm. The length of the item $L_0$ in Example 2 is 150 cm. Thus, all the visually detectable elements have the length different from the length of the item, wherein the length of the visually detectable elements is smaller than the length of the item.

The circumference of the roll is $$L = 120 \cdot 3 = 360 \text{ cm}$$

According to equation (4')

$$x = 360 - 2 \cdot 150 = 60 \text{ cm}$$

To calculate factor a, equation (5) is used:

$$N_3 = \frac{150 \text{ cm}}{60 \text{ cm}} \cdot a = \frac{5}{2} \cdot a$$

The smallest possible integer, i.e. factor a, needed to obtain the integer $N_3$ is 2.

Now, using equation (3), the number of items having different visually detectable features provided before the sequence of visually detectable features is repeated can be calculated:

$$Q = \frac{360}{60} \cdot 2 = 12$$

Figure 4:
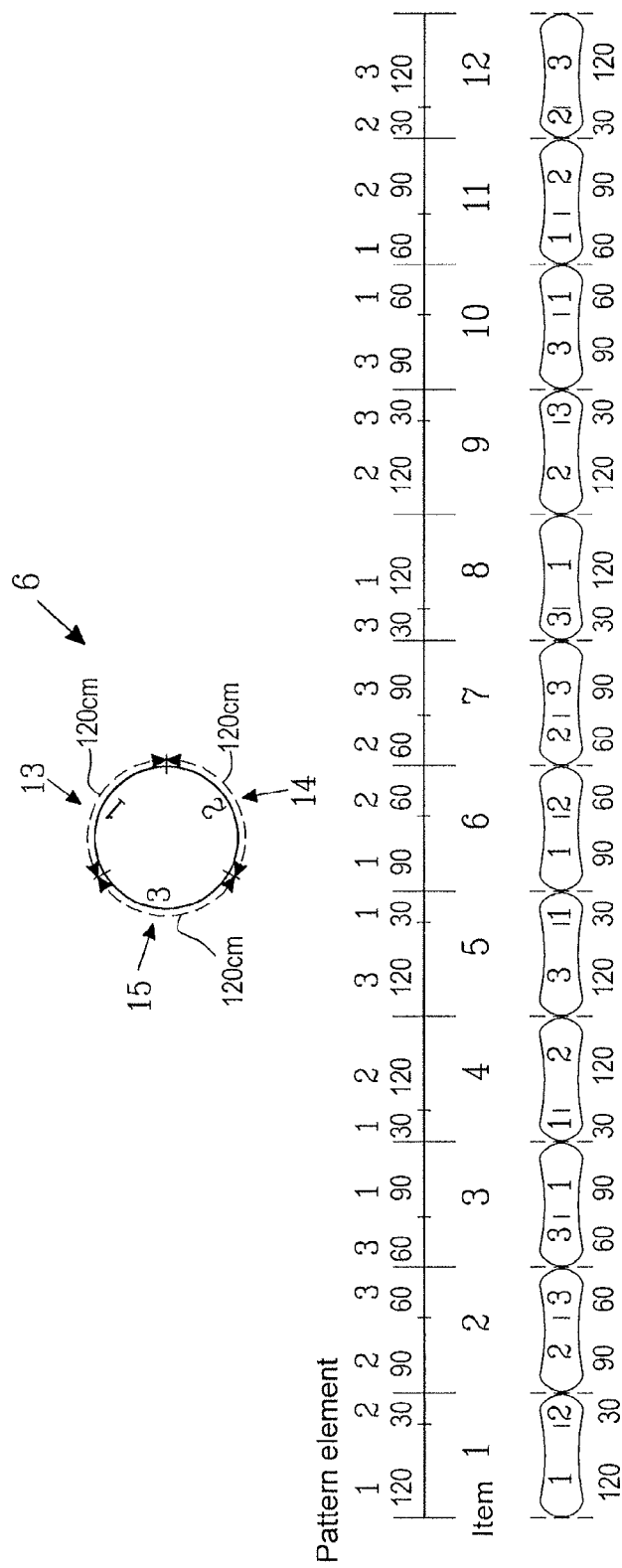

Indeed, as shown in FIG. 4, 12 items each having a different visually detectable feature are provided using the roll of Example 2.

Example 3

The roll of Example 3 includes two different visually detectable elements (16) and (17). As may be seen from FIG. 5, the visually detectable elements (16) and (17) have patterns designated 1 and 2 respectively, and all the visually detectable elements have a length of 200 cm. The length of the item $L_0$ in Example 3 is 150 cm. Thus, all the visually detectable elements have the length different from the length of the item, wherein the length of the visually detectable elements is greater than the length of the item.

The circumference of the roll is $$L = 200 \cdot 2 = 400 \text{ cm}$$

According to equation (4')

$$x = 400 - 2 \cdot 150 = 100 \text{ cm}$$

To calculate factor a, equation (5) is used:

$$N_3 = \frac{150 \text{ cm}}{100 \text{ cm}} \cdot a = \frac{3}{2} \cdot a$$

The smallest possible integer, i.e. factor a, needed to obtain the integer $N_3$ is 2.

Now, using equation (3), the number of items having different visually detectable features provided before the sequence of visually detectable features is repeated can be calculated:

$$Q = \frac{400}{100} \cdot 2 = 8$$

Figure 5:
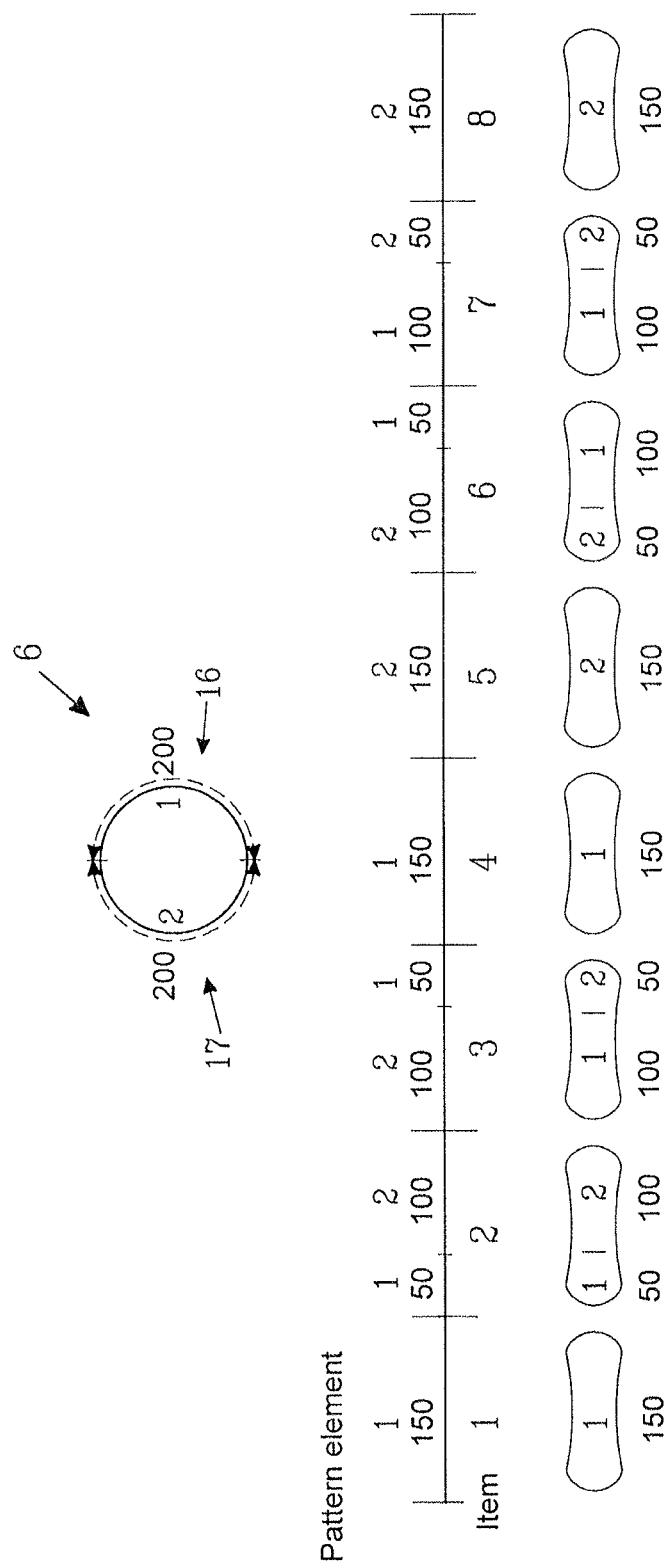

Indeed, as shown in FIG. 5, 8 items each having a different visually detectable feature are provided using the roll of Example 3.

Example 4

The roll of Example 4 includes two different visually detectable elements (18) and (19). As may be seen from FIG.

6, the visually detectable elements (18) and (19) have patterns designated 1 and 2 respectively, and all the visually detectable elements have a length of 60 cm. The length of the item $L_0$ in Example 4 is 150 cm. Thus, all the visually detectable elements have the length different from the length of the item, wherein the length of the visually detectable elements is smaller than the length of the item. Also, the circumference of the roll in Example 4 is smaller than the length of the item, i.e. $L<L_0$.

The circumference of the roll is $L = 60 \cdot 2 = 120$ cm

According to equation (4")

$x = 150 - 120 = 30$ cm

To calculate factor a, equation (5) is used:

$$N_3 = \frac{150 \text{ cm}}{30 \text{ cm}} \cdot a = 5 \cdot a$$

Since in this particular case 150/30 is an integer, factor a is 1.

Now, using equation (3), the number of items having different visually detectable features provided before the sequence of visually detectable features is repeated can be calculated:

$$Q = \frac{120}{30} \cdot 1 = 4.$$

Figure 6:
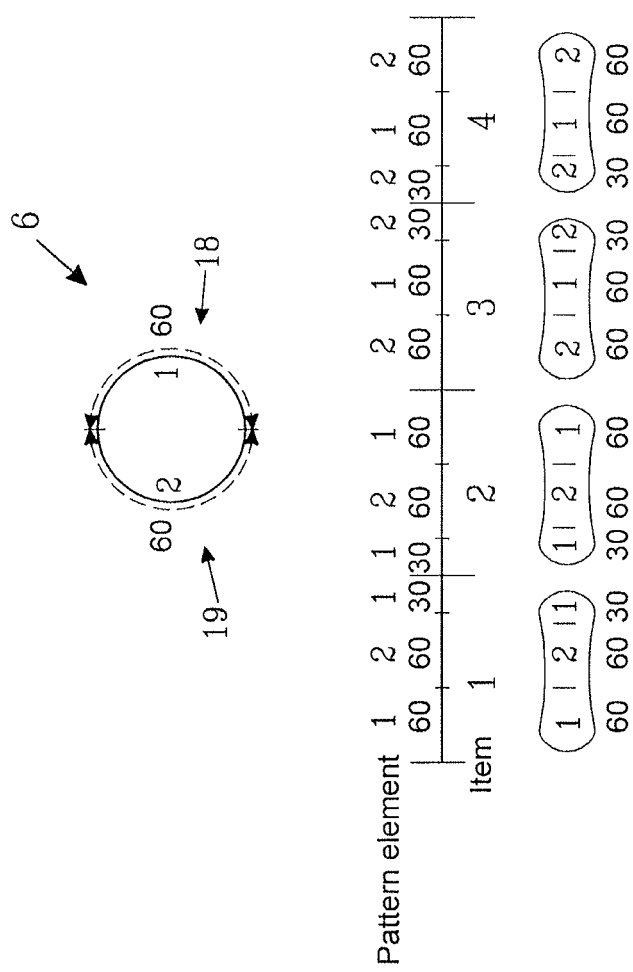

Indeed, as shown in FIG. 6, 4 items each having a different visually detectable feature are provided using the roll of Example 4.

Example 5

The roll of Example 5 includes three different visually detectable elements (20), (21) and (22). As may be seen from FIG. 7, the visually detectable elements (20), (21) and (22) have patterns designated 1, 2 and 3 respectively, wherein two of the visually detectable elements have a length of 50 cm, and the third visually detectable element have a length of 10 cm. The length of the item $L_0$ in Example 5 is 150 cm. Thus, all the visually detectable elements have the length different from the length of the item, wherein the length of the visually detectable elements is smaller than the length of the item. Also, the circumference of the roll in Example 5 is smaller than the length of the item, i.e. $L<L_0$.

The circumference of the roll is $L = 50 \cdot 2 + 10 = 110$ cm

According to equation (4")

$x = 150 - 110 = 40$ cm

To calculate factor a, equation (5) is used:

$$N_3 = \frac{150 \text{ cm}}{40 \text{ cm}} \cdot a = \frac{15}{4} \cdot a$$

The smallest possible integer, i.e. factor a, needed to obtain the integer $N_3$ is 4.

Now, using equation (3), the number of items having different visually detectable features provided before the sequence of visually detectable features is repeated can be calculated:

$$Q = \frac{110}{40} \cdot 4 = 11$$

Figure 7:
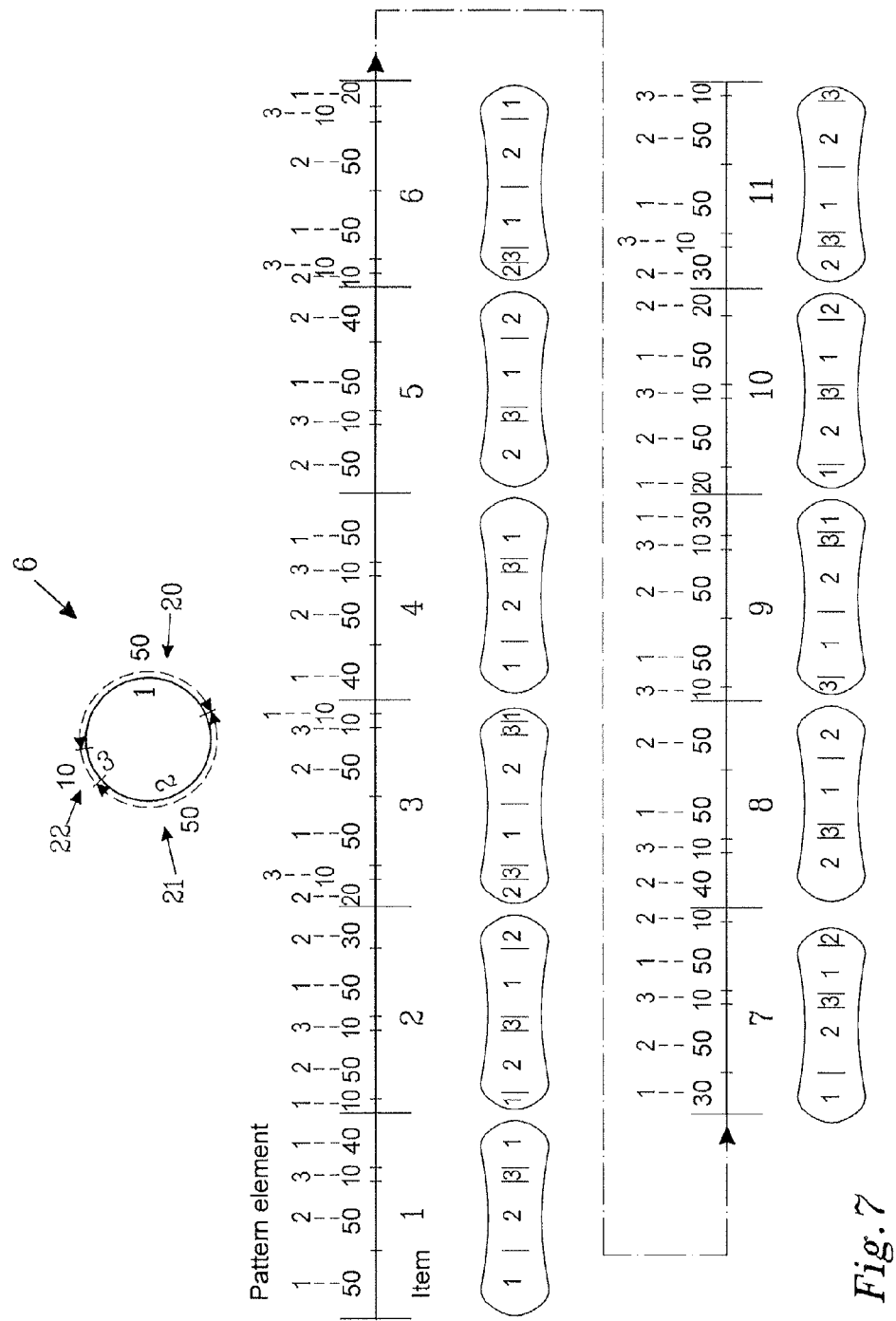

Indeed, as shown in FIG. 7, 11 items each having a different visually detectable feature are provided using the roll of Example 5. As may be understood, the smaller the visually detectable elements, the larger number of items each having a different visually detectable feature is provided.

Example 6

The roll of Example 6 includes two different visually detectable elements (23) and (24). As may be seen from FIG. 8, the visually detectable elements (23) and (24) have patterns designated 1 and 2 respectively, wherein all the visually detectable elements have a length of 111 cm. The length of the item $L_0$ in Example 6 is 150 cm. Thus, all the visually detectable elements have the length different from the length of the item, wherein the length of the visually detectable elements is smaller than the length of the item. The circumference of the roll in Example 6 is greater than the length of the item, i.e. $L>L_0$.

The circumference of the roll is $L = 111 \cdot 2 = 222$ cm

According to equation (4')

$x = 222 - 150 = 72$ cm

To calculate factor a, equation (5) is used:

$$N_3 = \frac{150 \text{ cm}}{72 \text{ cm}} \cdot a = \frac{25}{12} \cdot a$$

The smallest possible integer, i.e. factor a, needed to obtain the integer $N_3$ is 12.

Now, using equation (3), the number of items having different visually detectable features provided before the sequence of visually detectable features is repeated can be calculated:

$$Q = \frac{222}{72} \cdot 12 = 37$$

Figure 8:
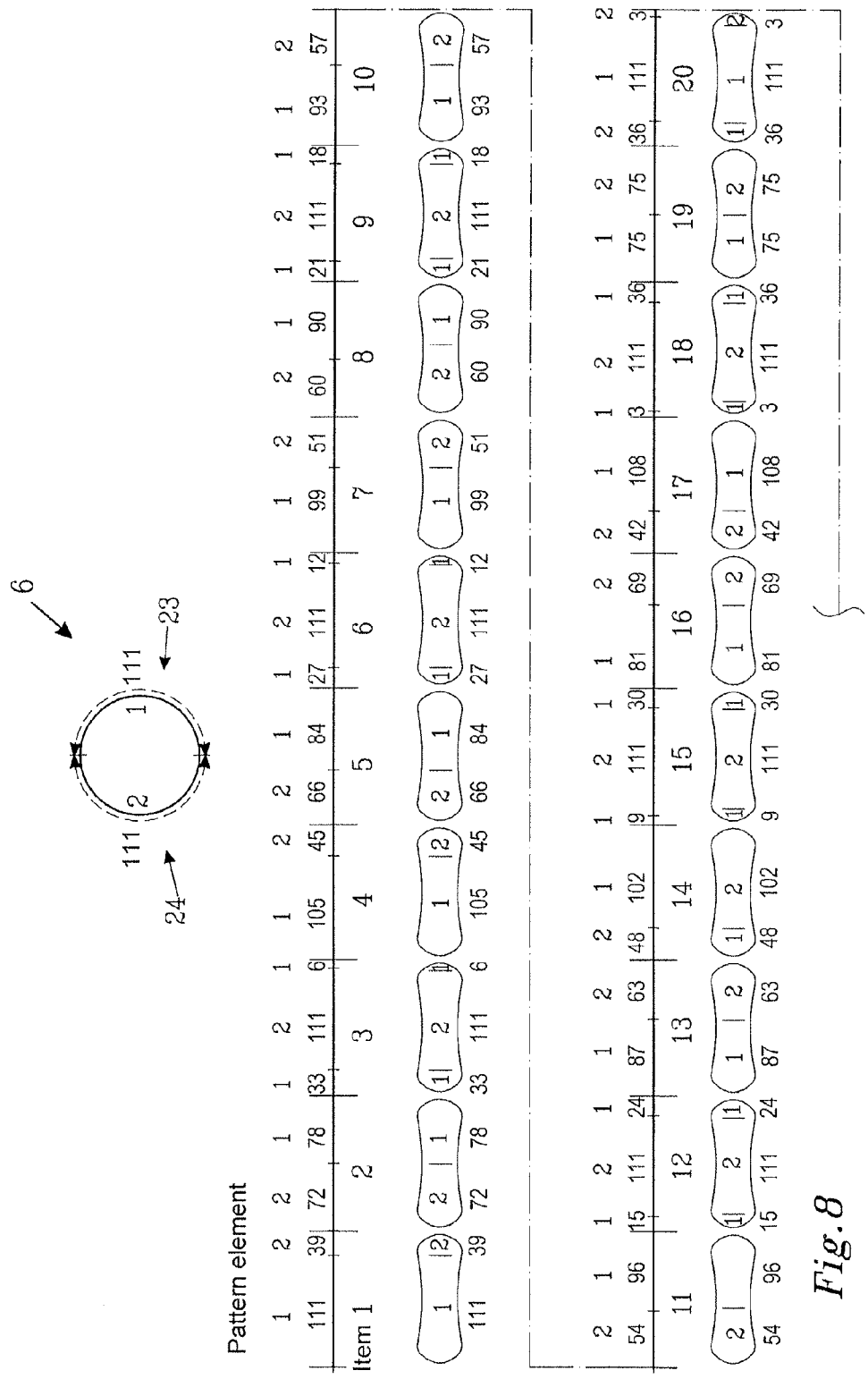

Indeed, as shown in FIG. 8, 37 items each having a different visually detectable feature are provided using the roll of Example 6.

As may be seen from the Examples above, the number of items each having a different visually detectable feature provided before the visually detectable features start to repeat themselves is significantly greater than the number of items provided by one full turn of the roll. In other words, a large number of items each having a different visually detectable feature may be provided using a roll having relatively small circumference.

Although the present invention has been described with reference to various embodiments, those skilled in the art will recognise that changes may be made without departing from the scope of the invention. It is intended that the detailed description be regarded as illustrative and that the appended claims including all the equivalents are intended to define the scope of the invention.

The invention claimed is:

1. A method of continuously imparting different visually detectable printed and/or embossed features to a plurality of items selected from the group consisting of an absorbent article; a wrapping sheet; and a release liner, said method comprising:
    providing a plurality of items for imparting said different visually detectable printed and/or embossed features;
    providing a roll comprising a plurality of visually detectable elements;
    imparting said visually detectable printed and/or embossed features to said plurality of items with said visually detectable elements on said roll,
wherein the circumference of the roll satisfies the following formula:

$$L \neq N_1 \cdot L_0 \quad (1)$$

wherein L is the circumference of the roll (6), $N_1$ is an integer and $L_0$ is the length of one item (1); and
wherein, in a production series, the number of items each having a different visually detectable printed and/or embossed feature provided before said visually detectable printed and/or embossed features repeat themselves is greater than n, wherein n is calculated as:

$$n = \frac{L}{L_0}. \quad (2)$$

2. The method according to claim 1, wherein said roll comprises at least one first visually detectable element having a length equal to the length of the item, and at least one second visually detectable element having a length different from the length of the item, wherein said first and said second visually detectable elements are different.

3. The method according to claim 1, wherein said roll comprises at least one first visually detectable element having a length different from the length of the item, and at least one second visually detectable element having a length different from the length of the item, wherein said first and said second visually detectable elements are different.

4. The method according to claim 1, wherein said roll is an embossing roll and/or a printing roll.

5. The method according to claim 1, wherein said visually detectable feature is a printed and/or embossed pattern, a printed and/or embossed image, a colour or a combination thereof.

6. The method according to claim 1, wherein in said production series, the number of items Q each having a different visually detectable feature provided before said visually detectable features repeat themselves is calculated as:

$$Q = \frac{L}{x} \cdot a \quad (3)$$

$$x = L - N_2 \cdot L_0 \text{ if } L > L_0 \quad (4')$$

$$x = L_0 - L \text{ if } L < L_0 \quad (4'')$$

$$N_3 = \frac{L_0}{x} \cdot a \quad (5)$$

$$N_2 = \left\lfloor \frac{L}{L_0} \right\rfloor \quad (6)$$

wherein L is the circumference of the roll, $N_2$ and $N_3$ are integers, $L_0$ is the length of one item, and a is the smallest integer needed to satisfy equation (5).

7. The method according to claim 1, wherein in said production series, a first item comprises a first visually detectable feature being provided by at least a portion of a first visually detectable element on said roll, and a second item in said production series comprises a second visually detectable feature being provided by at least a portion of said first visually detectable element on said roll, wherein said first and second visually detectable features are different.

8. The method according to claim 1, wherein said visually detectable feature is provided on at least one component of said absorbent article, wherein said component of said absorbent article is selected from the group consisting of a topsheet, a backsheet, an acquisition layer, and an absorbent element.

9. The method according to claim 1, wherein said visually detectable feature is provided on at least two components of said absorbent article, said visually detectable feature on the first component being different from said visually detectable feature on the second component, wherein said components of said absorbent article are selected from the group consisting of a topsheet, a backsheet, an acquisition layer, and an absorbent element.

* * * * *